United States Patent [19]

Jones

[11] 4,248,224
[45] Feb. 3, 1981

[54] DOUBLE VENOUS CANNULA

[76] Inventor: James W. Jones, 4108 James Dr., Metairie, La. 70003

[21] Appl. No.: 929,999

[22] Filed: Aug. 1, 1978

[51] Int. Cl.³ .................. A61M 1/03; A61M 5/00
[52] U.S. Cl. ...................... 128/214 R; 128/348; 128/DIG. 3; 128/350 R
[58] Field of Search ............ 128/214 R, 214.4, 348, 128/349 R, 350 R, 351 R, DIG. 3, 130

[56] References Cited

U.S. PATENT DOCUMENTS

| | | | |
|---|---|---|---|
| 2,935,068 | 5/1960 | Donaldson | 128/348 |
| 3,372,695 | 3/1968 | Beliveau et al. | 128/130 X |
| 3,490,456 | 1/1970 | Kortum | 128/348 |
| 3,683,911 | 8/1972 | McCormick | 128/214 R |
| 3,851,646 | 12/1974 | Sarns | 128/214 R |
| 4,043,346 | 8/1977 | Mobley et al. | 128/349 R |
| 4,072,153 | 2/1978 | Swartz | 128/350 R |
| 4,114,618 | 9/1978 | Vargas | 128/214.4 |
| 4,129,129 | 12/1978 | Amrive | 128/214 R |

OTHER PUBLICATIONS

Maraist et al., "Experimental Cardiac Surgery", *Surgery*, vol. 31, No. 1, Jan. 1952, pp. 146–153.
Campbell et al., "Cardiac Bypass in Humans", *Surgery*, vol. 40, No. 2, Aug. 1956, pp. 365–370.

*Primary Examiner*—Dalton L. Truluck
*Attorney, Agent, or Firm*—Keaty, Keaty & Garvey

[57] ABSTRACT

A venous cannula apparatus is comprised of a fluid conveying tube, the tube providing an upper tube portion which communicates with a pair of lower connected tube branch members. Each of the lower tube branches is normally in an angular position with respect to the upper tube, thus allowing the tube branches to coincide with the atrium, superior vena cava and inferior vena cava during an operation requiring a cardio pulmonary bypass. In the preferred embodiment, two flexible lower branch members are provided forming a "wye" or "tee" with the upper tube portion. The entire cannula structure is manufactured of a material having a "memory" so that after a flexure of the branch members, they return to their operative or normal "tee" or "wye" position. A substantially stiffened sleeve member is cooperatively associated with and connectable to the fluid conveying tube, the sleeve being slideable about the tube and being capable of urging the lower tube branches into an aligned position with the upper tube portion. The apparatus can be utilized during a cardiopulmonary bypass, with only a single opening being formed in the atrium. The cannula apparatus is operatively inserted through an opening surgically formed in the atrium. Removal thereafter of the sleeve allows the branch members to diverge and insert respectfully into the superior and inferior vena cava. Closures form substantially fluid tight seals between the cannula structure and the heart before bypass begins.

19 Claims, 6 Drawing Figures

U.S. Patent  Feb. 3, 1981  Sheet 1 of 3  4,248,224
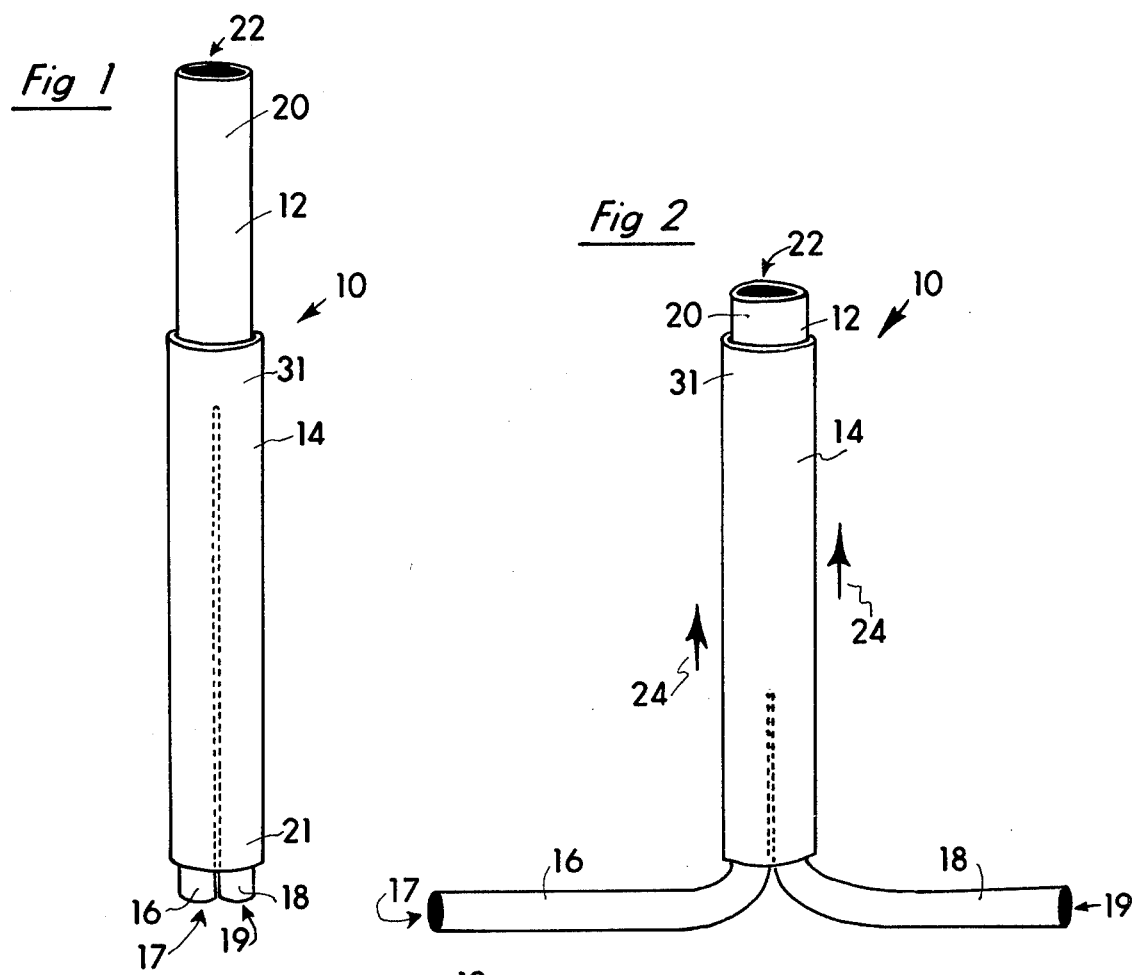
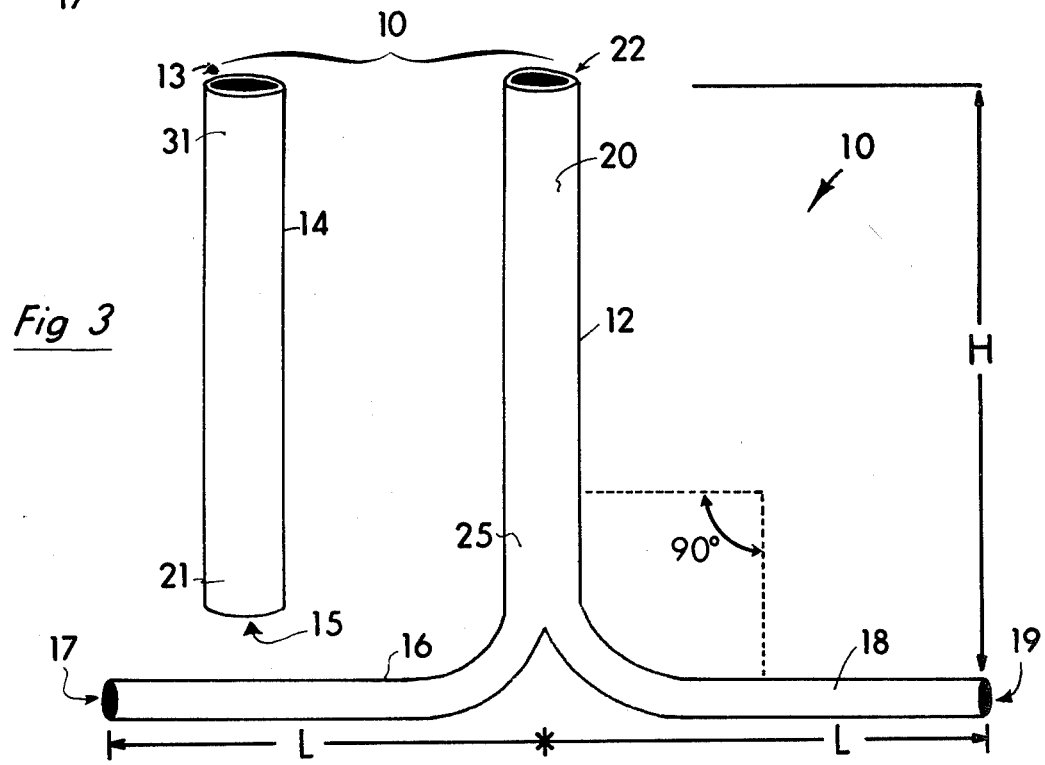

DOUBLE VENOUS CANNULA

BACKGROUND OF THE INVENTION

1. Field of the Invention

The present invention relates to medical and surgical tubes, and more particularly relates to cannulae and venous cannula and the like, as used in cardio-pulmonary bypass operations. Even more particularly the present invention relates to a venous cannula apparatus and its method of installation wherein a single cannula structure mounted in a single opening with a purse string, for example, closure provides branch tube members forming fluid connections with the superior and inferior vena cava.

2. General Background and Prior Art

When a surgeon places a patient on a cardio-pulmonary bypass machine, there is required a fluid connection between the heart and the machine. The machine circulates both blood returning from the body to the heart, termed the venous return, and blood pumped into the body from the heart-lung machine, termed the arterial outflow. The venous return is normally collected by a flexible tube, or several flexible tubes which is/are known in the art as a cannula(e) or venous cannula(e). The cannula is fed through an opening in the artium which opening is formed by the surgeon. The surgeon provides a "purse string" suture for example to seal the cannula properly after it is placed through the opening. The lower portion of the ell-shaped cannula is inserted in a curved fashion into the superior or inferior vene cava.

Presently, two tubes are usually required since each must make an approximate ninety degree bend for its proper placement and operation. The placement of a "tee" or "wye" would not be possible since such a structure could not pass through a small purse string opening. Due to the desire to reduce trauma to the heart, two very small openings are thus made with a single substantially ell-shaped cannula being entered and placed through each respective surgical opening, one tube or cannula placed through the atrium to the inferior vena cava, the other being placed through a second respective opening into the superior vena cava.

After placement of the cannulae a substantially fluid tight seal is formed using the purse string suture about the surgical opening by utilizing snares or clamps around the inferior vena cava and superior vena cava to form fluid tight connections with the cannula tube and the respective vein.

The placement aforedescribed of two separate cannula structures still represents a serious trauma to the heart with two surgical openings being formed. The operative procedure of placing two cannulae in the atrium and superior and inferior vena cava consumes a significant amount of time.

3. General Description of the Present Invention

The present invention solves all the prior art problems and shortcomings in a simple and inexpensive manner. The present invention provides a cannula structure which is comprised of an upper fluid conveying tube having preferably two lower branch tube members which are normally urged to an angular tee-like position with respect to the upper tube portion of the cannula.

An outer slideable sleeve is fitted over the upper tube structure and slides up and down the cannula with respect to its central bore. The sleeve is substantially stiff and its movement along the upper tube to the lower tube branches urges the tube branch members into a substantial alignment with the upper fluid conveying tube. Thus, the sleeve urges the branch members of the cannula into an aligned "collapsed" position so the entire structure can be passed through a single suture opening as is desirable. The combined external diameter of the two tube branch members is substantially equal to the external diameter of the main fluid conveying tube. The outer sleeve provides an internal diameter slightly greater than the external diameter of the main fluid conveying tube. Thus a slideable fit is achieved (Note FIGS. 1 and 2). The sleeve then provides the maximum diameter of the cannula structure in its "collapsed" state which allows placement of the structure through a minimal diameter opening in the atrium (See FIG. 4A).

After placement of the lowermost portion of the aligned tube branch members through the single surgical opening, the surgeon can slowly remove the sleeve in an upward fashion with the two branch tubes (now inside the atrium) being urged by "memory" into their proper angular "operative" positions feeding the inferior and superior vena cava respectively. Clamps secure the branch tubes in these operative positions (See FIG. 4C).

Memory can be supplied to the branch members by utilizing a suitable plastic-like material which will cause each branch member to spring back into its tee-like orientation when the outer sleeve is removed.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein:

FIG. 1 is a perspective view of the preferred embodiment of the apparatus of the present invention illustrating the sleeve portion in a retaining position over the tube branches;

FIG. 2 is a perspective view of the perferred embodiment of the apparatus of the present invention showing the sleeve in a removed position with the branch members being urged into lateral "tee-like" orientation;

FIG. 3 is an exploded perspective view of the perferred embodiment of the apparatus of the present invention;

DETAILED DESCRIPTION OF THE PREFERRED EMBODIMENT

Figure 4A:
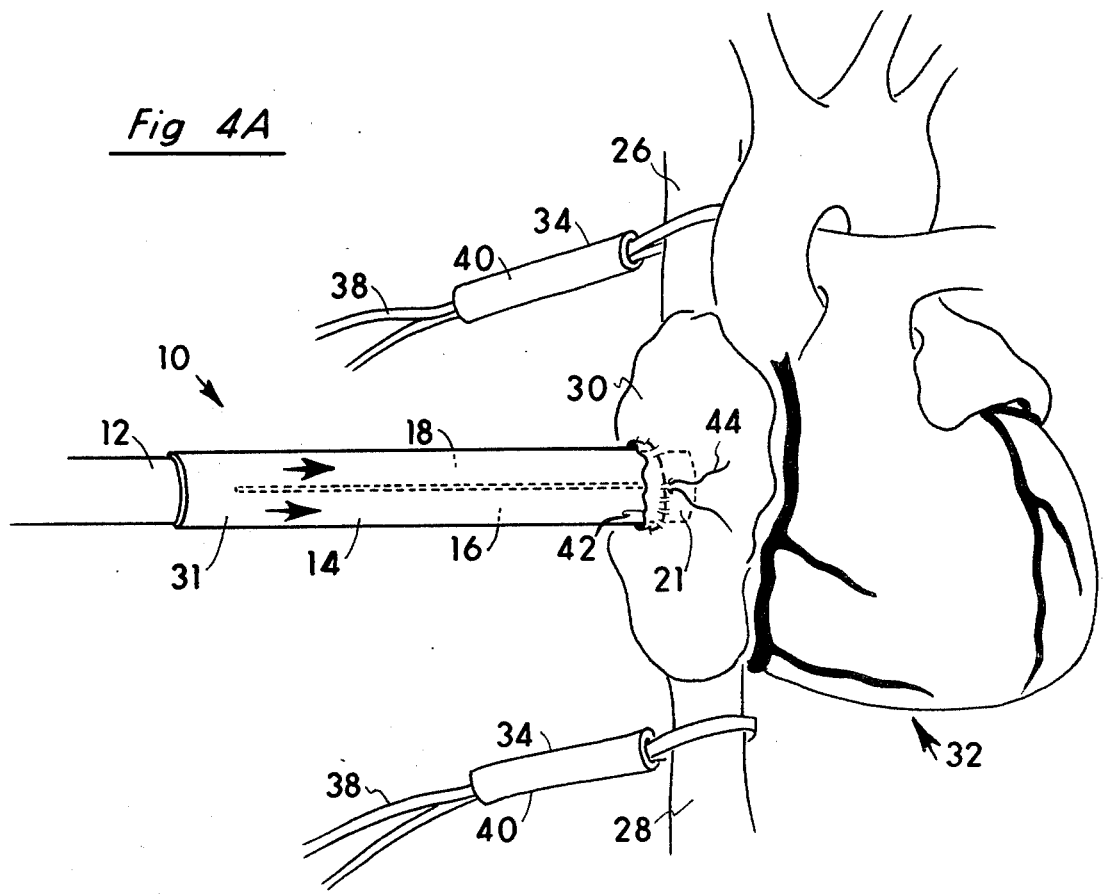
FIGS. 4A–4C are sequential views illustrating the installation of the preferred embodiment of the apparatus of the present invention into a human heart prior to a cardio-pulmonary bypass operation.

FIG. 1 best illustrates the perferred embodiment of the apparatus of the present invention designated generally by the numeral 10.

In FIG. 1 there can be seen an upper tube 12 which is, for example, a fluid conveying cylindrical tube having an upper 20 tube portion and a lower or distal tube portion which is comprised of a right lower tube branch 18 and a left lower tube branch 16.

Further provided in FIG. 1 can be seen a sleeve 14 which slideably and moveably fits over upper tube 12. Sleeve 14 is provided with a proximal end portion 31 and a lower distal end portion 21.

A proximate opening 22 is provided at the upper portion 20 of tube 12.

Openings 17, 19 are provided at lower tube branch 16 and lower tube branch 18 respectively. It should be understood that a continuous inner open bore is provided through the central portion of tube 12 and branch tubes 16, 18 providing a communication between opening 22 and openings 17, 19. Thus, fluid introduced into opening 22 could flow through the center portion of tube 20 and exit at openings 17, 19. Likewise fluid entering openings 17, 19 would flow through branch tubes 16, 18 and into tube 12 exiting opening 22. Thus, a communicating fluid conveying tube is provided in tube 12 and branch tubes 16, 18.

Arrows 24, FIG. 2 illustrate the slideable movement of sleeve 14 along tube 12.

Note in FIG. 1 that sleeve 14 has moved to a first lowermost position coverably contacting branch tubes 16, 18 and urging them to an intermost "collapsed" position where each tube of branch 16, 18 is substantially aligned with tube 12. Sleeve 14 as seen in FIG. 1 provides an internal diameter slightly greater than the external diameter of tube 12, and slightly greater than the combined external diameter of branch tube members 16, 18. It can be seen from the above that the external diameter of sleeve 14 thus provides the maximum external diameter when cannula 10 is in its "collapsed" position as seen in FIG. 1. Further, the external diameter of sleeve 10 controls the diameter of an opening 42 formed in the atrium.

This is desirable, because the entire cannula structure 10 can then be placed through a single small opening 42 formed by the surgeon in the atrium 30 of the heart (See FIG. 4A), thus minimizing trauma.

In FIG. 2, as indicated by arrows 24 sleeve 14 has been moved to an uppermost position, removed from the branch tubes 16, 18, with tubes 16, 18 assuming their lateral operative position. Branch tubes 16, 18 and tube 20 would preferably be manufactured of a suitable flexible material, but of a meterial which would have a "memory". Thus, when tubes 16, 18 are bent they will return to their original manufactured and cast position. Alternatively, resilient springs could be provided within the walls of tube branches 16, 18 and tube 12.

In FIG. 2, tubes 16, 18 have returned to a "tee-like" position, this position further being illustrated in FIG. 3. Note that the removal of sleeve 14 from its adjacent coverable position over to branches 16, 18 as is shown in FIG. 1 causes each tube 16, 18 to assume this tee-like lateral position as is desirable.

Figure 4B:
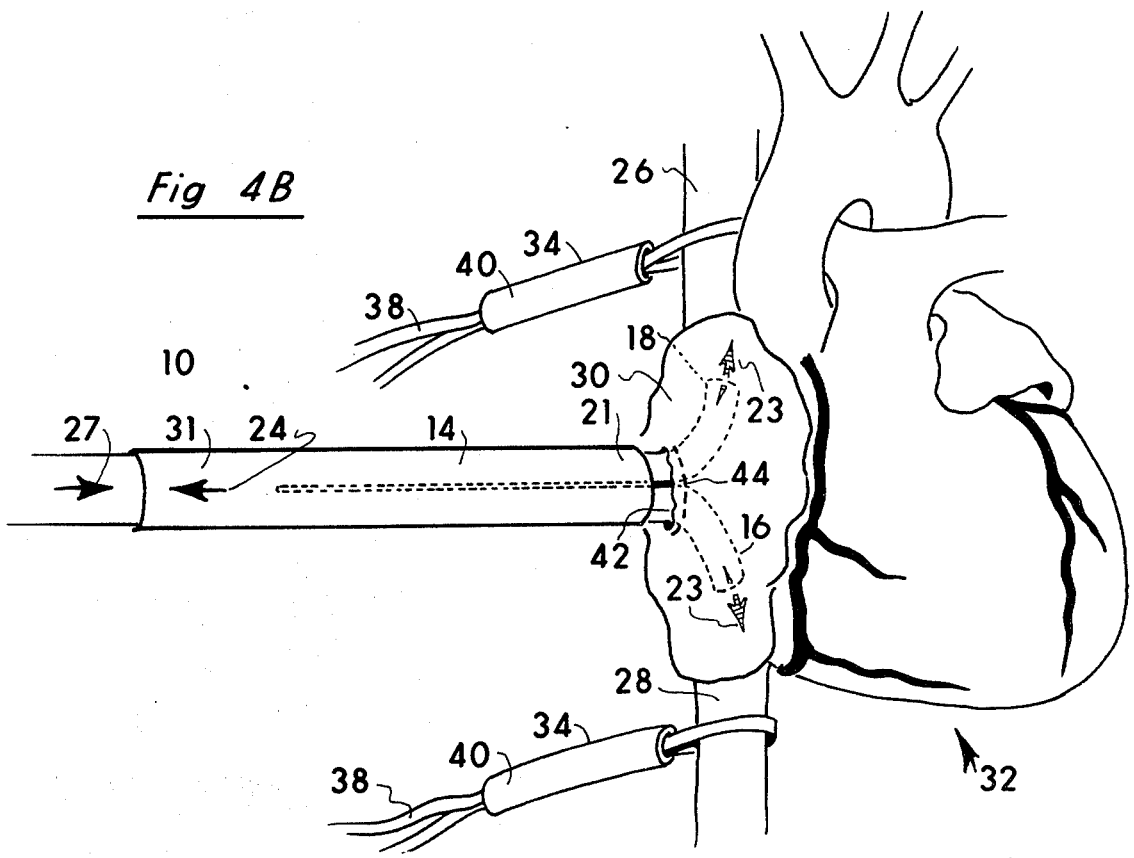
Figure 4C:
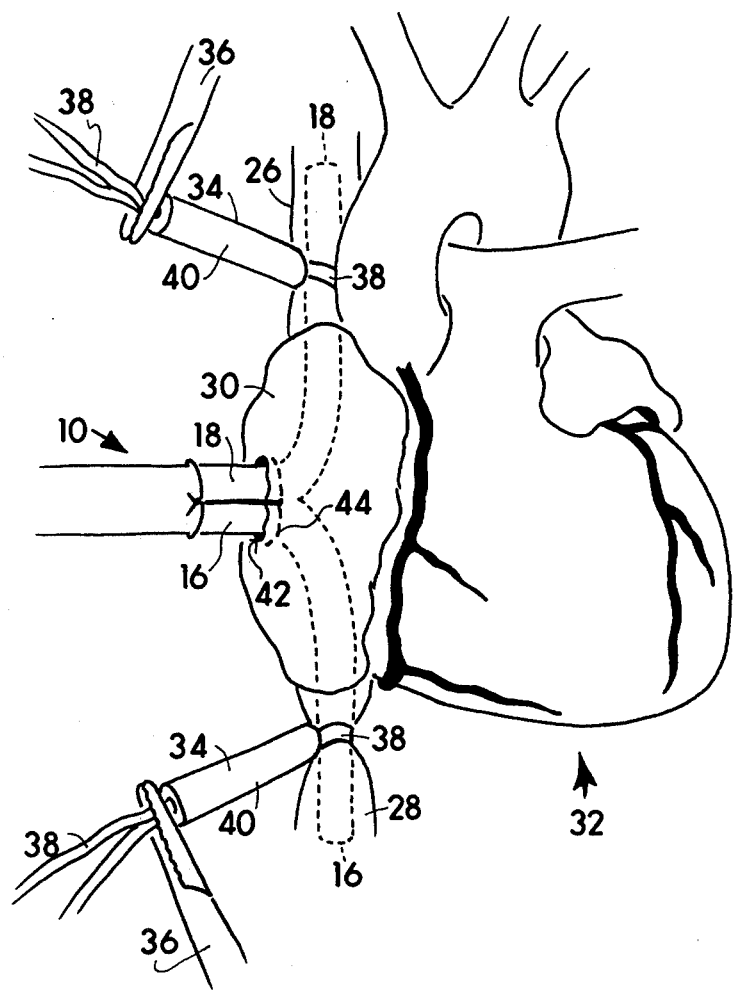

As will be described more fully hereinafter, the removal of sleeve 14 allows each tube branch 16, 18 to be placed laterally into the superior 28 or inferior 26 vena cava respectively (FIG. 4C).

In FIG. 3, there is provided an exploded view of the cannula apparatus 10 of the present invention showing the sleeve 14 removed from tube 12. In the preferred embodiment each tube of branch 16, 18 is provided in a length L which length would be sufficient to allow the tube branch members 16, 18 to sufficiently penetrate and enter the superior and inferior vena cava when the entire assembly of cannula 10 is placed through a purse string opening 42 in the atrium portion 30 of heart 32.

Likewise, tube 12 should be provided with a sufficient height H as to allow the tube branch members 16, 18 to fully occupy and implant themselves within the superior and inferior vena cava (28, 26 respectively) while still leaving the upper portion 20 of tube 12 for the connection of opening 22 to a heart lung machine or the like.

In FIG. 3, a ninety degree angular orientation of each tube branch members 16, 18 is provided. It should be understood however, that other suitable angular orientations of tube branch members 16, 18 with respect to tube 12 could be provided to fit particular anatomical applications.

FIGS. 4A–4C illustrate the method of installation of cannula 12 within the teaching of the present invention.

In FIG. 4A, sleeve 14 has been movably slided to a position (See arrows FIG. 4A) adjacent and covering branch tube members 16, 18. Note that the branch members 16, 18 have been urged into a substantially aligned position with tube 12. In this position the entire cannula apparatus 10 provides a substantially constant diameter D which can pass through the opening 42 formed by the surgeon.

In FIG. 4A, the surgeon has formed an opening 42 in the atrium 30 portion of heart 42. It can be seen that the lowermost end portion 21 of sleeve 14 has penetrated the atrium 30 through opening 42. A purse string or like suitable closure 44 is provided for forming a sealable substantially fluid tight connection sealing the atrium 30 to the walls of sleeve 14 and cannula 10.

In FIG. 4B, sleeve 14 is moved upwardly by the surgeon (See arrow 24) while the surgeon simultaneously pushes the tube 12 portion of cannula 10 downward (See arrow 27). As each tube branch member 16, 18 "clears" the end portion 21 of sleeve 14, it diverges outwardly (See Arrow 23) toward the superior vena cava 28 and inferior vena cava 26 respectively. Since the material utilized to manufacture cannula 10 will be of a pliable yet firm material, having a "memory", the cannula tube branches 16, 18 will move towards superior vena cava 28 and inferior vena cava 26 as illustrated in FIG. 4B. A rough ninety degree orientation of each tube branch member is satisfactory. Also, branches 16, 18 will have some pliability which in combination with the pliability of the superior and inferior vena cava 23, 26 allows the surgeon to manipulate each branch 16, 18 into its respective vena cava 23, 26 as is illustrated in FIGS. 4B and 4C.

In FIG. 4C, each tube branch members 16, 18 of cannula 10 has fully diverged to its respective vena cava 28, 26. Note that clamps 34 would have been utilized to form substantially fluid tight connections between the vena cava and the cannula tube branch wall. Rummel type tourniquets could be utilized which are comprised generally of a umbilical tape tension member 38, an annular rubber tubing sleeve 40 and a homestat 36. Such "Rummel type" tourniquets are known in the art.

In FIG. 4C, sleeve 14 has been removed as cannula 10 has assumed its operative "tee-like" position. The surgeon then tightens his purse string or like connection 44 to secure a fluid tight connection between the atrium 30 and cannula 10.

Cannula 10 should be manufactured of a material that preserves the tube lumen, reducing the chance for collapse of the tube during operation. Further, an FDA approved material for use as surgical tubing such as any number of plastics could be used including polyvinyl chloride and the like.

What is claimed as invention is:

1. A cardio pulmonary bypass venous cannula apparatus, comprising:
   a. a fluid conveying tube, said tube providing an upper proximate tube portion communicating with a pair of lower distal tube branch members, each of said lower distal tube branch members being movable into an angular lateral position with respect to said upper tube with one of said tube branch members being insertable into the inferior vena cava and the other of said tube branch members being insertable into the superior vena cave;

b. means slideably surrounding the exterior surface of said tube branch members for urging each of said lower distal tube branches into a collapsed aligned position with said upper tube portion allowing said distal tube branches to be inserted through a single surgical opening in the atrium of a patient during a cardio pulmonary bypass; and c. closure means associated with said upper tube for forming a substantially fluid tight enclosure between said upper proximate tube portion and the walls of the single surgical opening into which said tube is inserted during the cardio pulmonary bypass.

2. The venous cannula apparatus of claim 1 wherein each of said tube branch members normally assumes an angular "tee-like" lateral position with respect to said fluid conveying tube.

3. The venous cannula apparatus of claim 1 wherein said tube branch members are of a material having a memory wherein said tube branch members will return to their original position after being flexed.

4. The venous cannula apparatus of claim 3 wherein said urging means a sleeve member movably attached to the outer portion of said fluid conveying tube.

5. The venous cannula apparatus of claim 4 wherein each of said tube branch members is normally laterally deposed with respect to said tube body.

6. The venous cannula apparatus of claim 5 wherein said sleeve member is cylindrical sleeve having an internal diameter equal to or greater than the combined external diameters of said tube branch members.

7. The venous cannula apparatus of claim 4 wherein said sleeve member provides the maximum diameter to said venous cannula apparatus when said branch tube members are urged to said collapsed aligned position.

8. A venous cannula apparatus, comprising:
a. cylindrical fluid conveying tube, said tube providing an upper tube portion communicating with a pair of cylindrical lower tube branch members connected to said fluid conveying tube and said lower tube branch members are of a combined external diameter substantially equal to the external diameter of said fluid conveying tube, and each of said lower tube branch members normally assumes a lateral operative position with respect to said fluid conveying tube, and each of said lower tube branch members are adapted to fit within the superior and inferior vena cava of a patient during coronary bypass surgical operation;

b. a cylindrical annular sleeve fittable over said fluid conveying tube and said pair of cylindrical lower tube branch members in a slidable fashion, said sleeve being slideably movable over said tube and said tube branch members from a first aligned collapsed position to a second removed operative postion, each of said branch members being substantially aligned with said fluid conveying tube and said sleeve when said sleeve assumes said first aligned position, said cannula apparatus further providing a maximum external diameter substantially equal to the external diameter of said fluid conveying tube, said maximum diameter adapted to pass through a formed surgical opening when said sleeve assumes said collapsed position, each of said tube branch members being extendable laterally into the superior and inferior vena cava respectively during a surgical bypass of the heart when said sleeve assumes said second removed operative position; and c. a pair of clamp members for forming a substantially fluid tight seal between each of said tube branch members and the superior and inferior vena cava respectively.

9. The venous cannula apparatus of claim 8 wherein each of said clamp member is comprised of a tensile flexible tape member, an annular tubing sleeve covering the end portions of said tape and a clamp instrument securing the end portions of said tape within said tubing member.

10. The venous cannula apparatus of claim 8, further comprising closure means associated with said upper tube for forming a substantially fluid tight enclosure between said upper tube portion and the walls of a single surgically formed opening in the atrium of a heart.

11. The venous cannulae apparatus of claim 8 wherein each of said tube branch members are flexible and have a memory, allowing each tube to return to its original lateral position after being temporarily bent.

12. The venous cannula apparatus of claim 8 wherein each of said tube branch members is normally oriented at generally ninety degrees with respect to said upper tube portion.

13. A method of forming a cardio pulmonary bypass surgical connection comprising the steps of:
a. forming a single opening in the atrium portion of the heart;
b. providing a fluid conveying y-cannula having an upper tube and a pair of depending branch tubes integrally connected thereto, the upper tube defining a proximate end portion of the y-cannula and the branch tubes defining a distal end portion thereof;
c. substantially surrounding the y-cannula with an external sleeve;
d. inserting the distal branched end portion of the y-cannula and surrounding sleeve into the formed single opening;
e. withdrawing the sleeve from the branch tubes allowing them to diverge laterally within the atrium;
f. placing the end portion of one of the branch tubes into the superior vena cava;
g. placing the end portion of the second of the branch tubes into the inferior vena cava;
h. forming a substantially fluid tight connection at the single opening between the atrium and the proximate end portion of the y-cannula.

14. The method of claim 13 further comprising the step of securing an end portion of each respective fluid conveying tube to the superior vena cava and inferior vena cava respectively.

15. A method of forming a coronary bypass surgical connection comprising the steps of:
a. forming a single opening in the atrium portion of the heart;
b. providing a pair of elongated fluid conveying cannulae;
c. placing a sleeve about the pair of fluid conveying cannulae at the single formed surgical opening;

d. inserting the distal end portion of the combined sleeve and cannulae into the formed single opening;

e. diverging the pair of fluid conveying cannulae from the sleeve distal end portion respectively toward the superior vena cava and the inferior vena cava;

f. placing the end portion of one of the fluid conveying cannulae into the superior vena cava;

g. placing the end portion of the second of the fluid conveying cannulae into the inferior vena cava; and h. forming a substantially fluid tight connection at the single opening between the atrium and the fluid conveying tubes.

16. The method of claim 15 further comprising the step of forming a seal around each cannulae and its respective vena cava with blood flow in the respective vena cava being thereafter through the respective cannulae.

17. The method of claim 15 wherein the step "b" each cannula is connected to an upper tube portion with fluid flow from each cannula being into said upper tube.

18. The method of implanting a cannula apparatus in a heart during a surgical cardio pulmonary bypass operation comprising the steps of:

a. providing a branched cannula apparatus which apparatus comprises a fluid conveying tube and a pair of connected normally laterally extending branch tube members;

b. urging the branch tube members into substantial alignment with the fluid conveying tube;

c. surrounding the aligned branch tube members with a sleeve;

d. forming a single opening in the atrium portion of the heart;

e. passing the lower tip portions of the tube branch members of the aligned cannula apparatus a distance through the formed opening and into the atrium;

f. allowing the branch tube members to diverge laterally within the atrium towards the superior and inferior vena cava respectively as the branch tube members exit the lower distal end of the sleeve; and g. securing each tube branch member within the superior and inferior vena cava respectively in a substantially fluid tight fashion.

19. The method of claim 10 further comprising the step of forming a substantially fluid tight seal between the fluid conveying tube and the atrium portion of the heart at the formed opening.

* * * * *